(12) United States Patent
Endo

(10) Patent No.: US 8,705,840 B2
(45) Date of Patent: Apr. 22, 2014

(54) DEFECT INSPECTION DEVICE AND DEFECT INSPECTION METHOD

(75) Inventor: Kazumasa Endo, Kawasaki (JP)

(73) Assignee: Nikon Corporation, Tokyo (JP)

( * ) Notice: Subject to any disclaimer, the term of this patent is extended or adjusted under 35 U.S.C. 154(b) by 136 days.

(21) Appl. No.: 13/096,490

(22) Filed: Apr. 28, 2011

(65) Prior Publication Data

US 2011/0249112 A1    Oct. 13, 2011

Related U.S. Application Data

(63) Continuation of application No. PCT/JP2009/068454, filed on Oct. 28, 2009.

(30) Foreign Application Priority Data

Oct. 31, 2008   (JP) .................................. 2008-282075

(51) Int. Cl.
*G06K 9/00*   (2006.01)
(52) U.S. Cl.
USPC ........................................................ 382/145
(58) Field of Classification Search
USPC ......................................... 382/141, 145, 152
See application file for complete search history.

(56) References Cited

U.S. PATENT DOCUMENTS

| | | | | |
|---|---|---|---|---|
| 5,583,609 | A * | 12/1996 | Mizutani et al. | 355/46 |
| 6,263,099 | B1 * | 7/2001 | Maeda et al. | 382/149 |
| 6,512,578 | B1 * | 1/2003 | Komatsu et al. | 356/237.5 |
| 2004/0042648 | A1 * | 3/2004 | Yoshidda et al. | 382/151 |
| 2006/0007436 | A1 | 1/2006 | Kurosawa et al. | |
| 2006/0159330 | A1 * | 7/2006 | Sakai et al. | 382/141 |
| 2007/0031025 | A1 * | 2/2007 | Lim et al. | 382/149 |
| 2008/0232674 | A1 * | 9/2008 | Sakai et al. | 382/149 |
| 2009/0147247 | A1 | 6/2009 | Endo et al. | |

FOREIGN PATENT DOCUMENTS

| | | |
|---|---|---|
| JP | 6-94631 | 4/1994 |
| JP | 7-333164 | 12/1995 |
| JP | 9-89794 | 4/1997 |
| JP | 2006-23221 | 1/2006 |
| JP | 3956042 | 5/2007 |
| JP | 3956042 | 5/2007 |
| JP | 2008-58248 | 3/2008 |
| WO | WO 2008/015973 | 7/2008 |

OTHER PUBLICATIONS

Chinese Office Action Issued Feb. 28, 2012 in corresponding Chinese Patent Application 200980142750.X (6 pages) (7 pages English translation).

* cited by examiner

*Primary Examiner* — Edward Park

(57) ABSTRACT

A defect inspection device and an inspection method which can decide the quality of a pattern shape of a sample surface in a short time are provided. A defect inspection device 20 that inspects a defect of a substrate (wafer 10) on which a repeated pattern is formed includes an illumination optical system 21 that has an objective lens 9 and radiates light from a light source 1 onto the repeated pattern formed on the wafer 10 via the objective lens 9, a detection optical system 22 that detects an image of a pupil plane of the objective lens 9 produced by diffracted light of a plurality of orders caused by the repeated pattern and a detection section 23 that detects a defect of the repeated pattern of the wafer 10 from the pupil image obtained.

19 Claims, 8 Drawing Sheets

| INSPECTION POINT | SEM | GRADATION VALUE R | GRADATION VALUE G | GRADATION VALUE B |
|---|---|---|---|---|
| No.1 | S1 | R1 | G1 | B1 |
| No.2 | S2 | R2 | G2 | B2 |
| No.3 | S3 | R3 | G3 | B3 |
| ... | ... | ... | ... | ... |
| No.n | Sn | Rn | Gn | Bn |
| CORRELATION COEFFICIENT WITH SEM | | CR(L,M) | CG(L,M) | CB(L,M) |

(b)

| AREA ON PUPIL SURFACE | GRADATION VALUE R | GRADATION VALUE G | GRADATION VALUE B |
|---|---|---|---|
| P(0, 0) | CR(0, 0) | CG(0, 0) | CB(0, 0) |
| P(1, 0) | CR(1, 0) | CG(1, 0) | CB(1, 0) |
| P(2, 0) | CR(2, 0) | CG(2, 0) | CB(2, 0) |
| ... | ... | ... | ... |
| P(N, N) | CR(N, N) | CG(N, N) | CB(N, N) |

US 8,705,840 B2

DEFECT INSPECTION DEVICE AND DEFECT INSPECTION METHOD

CROSS REFERENCE TO RELATED APPLICATIONS

This application is a continuation application, filed under 35 U.S.C. §111(a), of International Application PCT/JP2009/068454, filed Oct. 28, 2009, which claimed priority to Japanese Application No. 2008-282075, filed Oct. 31, 2008, the disclosures of which are hereby incorporated by reference.

TECHNICAL FIELD

The present invention relates to a defect inspection device and a defect inspection method.

BACKGROUND ART

Conventionally, a pattern formed on a resist layer on the surface of a semiconductor wafer or liquid crystal substrate (hereinafter referred to as "sample") is inspected for defects in manufacturing steps of a semiconductor circuit element or liquid crystal display element. For example, there is disclosed an inspection method which adjusts a polarization state of light from a light source and intensities of 0-th order and high-order diffracted light beams that form optical images and compares the images of the sample surface (e.g., see Patent Document 1). For such an inspection, Critical Dimension SEM (critical dimension scanning electron microscope, hereinafter referred to as "CD-SEM") is used.

CITATION LIST

Patent Literature

Patent Literature 1: Japanese Patent No. 3956942

SUMMARY OF INVENTION

Technical Problem

However, the inspection method using this CD-SEM has a problem with resist damages or a problem that such a method is unfit to inspect the total wafer surface from the standpoint of throughput.

The present invention has been implemented in view of the above described problems and it is an object of the present invention to provide a defect inspection device and a defect inspection method capable of deciding the quality of a pattern shape of a sample surface in a short time regardless of a resist pattern formed on the sample surface or a pattern after etching (inspection pattern).

Solution to Problem

In order to solve the above described problems, the defect inspection device according to the present invention is a defect inspection device that inspects a defect of a substrate on which a repeated pattern is formed, including a detection optical system including an objective lens that condenses light from the substrate, a receiver that receives diffracted light of a plurality of orders generated due to the repeated pattern of the substrate at a position where a pupil image generated at a pupil plane of the detection optical system is formed and a detector that detects a defect of the repeated pattern of the substrate based on a brightness of a portion of a detection region out of detection regions where the diffracted light of the receiver is detected.

In the defect inspection device, preferably, the portion of the detection region is a region of a pupil image generated by diffracted light of any one order out of the diffracted light of a plurality of orders.

Furthermore, it is preferable to adopt a configuration such that the defect inspection device includes a storage that stores a reference value, the detector reads the reference value from the storage, compares the reference value with the brightness calculated from the pupil image and detects a defect of the repeated pattern formed on the substrate.

Furthermore, in the defect inspection device, preferably, the portion of the detection region is a region where a correlation of a difference of the repeated pattern and the brightness is large, and the detection section is configured so as to detect a defect of the repeated pattern of the substrate according to the brightness at the portion of the detection region.

Furthermore, in the defect inspection device, preferably, for the portion of the detection region, a correlation between a measured value of an evaluation substrate on which a plurality of repeated patterns having different levels of quality are formed by reference measuring means and the brightness of the pupil image by diffracted light of a plurality of orders by the evaluation substrate for each order and determine a pupil image region by an order of diffracted light with the high correlation.

Furthermore, the defect inspection device preferably includes an illumination optical system including the objective lens that radiates light from a light source onto the repeated pattern formed on the substrate via the objective lens.

Furthermore, in the defect inspection device, the illumination optical system preferably includes a wavelength selector that selects a wavelength region of light from the light source radiated onto the repeated pattern formed on the substrate.

Furthermore, in the defect inspection device, the illumination optical system preferably includes a polarizer that polarizes the light from the light source radiated onto the repeated pattern formed on the substrate to a predetermined linear polarization state.

Furthermore, in the defect inspection device, the illumination optical system preferably includes an aperture stop at a position conjugate with the pupil plane and the aperture of the aperture stop is preferably configured to be enabled to change the position and aperture diameter within the plane orthogonal to the optical axis of the illumination optical system.

Furthermore, in the defect inspection device, the illumination optical system preferably includes an aperture stop at a position conjugate with the pupil plane and the illumination optical system is preferably configured so as to satisfy the condition of:

$$Ra \leq |\beta| \times f \times \lambda / P$$

where the length of the aperture of the aperture stop in the direction of a straight line connecting the optical axis of the illumination optical system and the aperture is Ra, imaging magnification between the aperture stop and pupil of the objective lens is $\beta$, wavelength of light radiated onto the repeated pattern formed on the substrate is $\lambda$, the pitch of the repeated pattern is P and the focal length of the objective lens is f.

Furthermore, the defect inspection method according to the present invention is a method of inspecting a defect of the substrate on which a repeated pattern is formed, including a receiving step of receiving diffracted light of a plurality of orders generated due to the repeated pattern at a position where a pupil image generated at a pupil plane of a detection optical system including an objective lens that condenses light from the substrate can be detected and a detection step of detecting a defect of the repeated pattern of the substrate based on a brightness at a portion of a detection region out of regions where the diffracted light of the plurality of orders is received in the receiving step.

In the defect inspection method, preferably, the portion of the detection region is a region of a pupil image generated by diffracted light of any one order out of the diffracted light of a plurality of orders.

Furthermore, in the defect inspection method, the detection step is preferably configured so as to compare a conforming reference value with a brightness obtained in the receiving step and detect a defect of the repeated pattern formed on the substrate.

Furthermore, in the defect inspection method, preferably, the portion of the detection region is a region where a correlation of a difference of the repeated pattern and the brightness is large, and the detection step is configured so as to detect a defect of the repeated pattern formed on the substrate according to the brightness of the portion of the detection region obtained in the receiving step.

In the defect inspection method, preferably, for the portion of the detection region, a correlation between a measured value of an evaluation substrate on which a plurality of repeated patterns having different levels of quality are formed by reference measuring means and the brightness of the pupil image by diffracted light of a plurality of orders by the evaluation substrate for each order and determine a pupil image region by an order of diffracted light with the high correlation.

Furthermore, the defect inspection method preferably includes an illumination step of radiating light from a light source onto the repeated pattern formed on the substrate via the objective lens prior to the receiving step.

Advantageous Effects of Invention

In accordance with the defect inspection device and defect inspection method according to the present invention, it is possible to decide the quality of a pattern shape of a sample surface in a short time regardless of a resist pattern of the sample surface or a pattern after etching.

BRIEF DESCRIPTION OF DRAWINGS

FIG. 5 is a diagram illustrating a configuration of a table for managing a relationship between a CD-SEM value of a test wafer and a gradation value of a pupil image measured using a defect inspection device; (a) illustrating a correspondence table storing the correspondence between a CD-SEM value and a gradation value per area of the pupil image and (b) illustrating a correlation function table storing a CD-SEM value and a correlation coefficient per area of the pupil plane.

DESCRIPTION OF EMBODIMENTS

Figure 1:
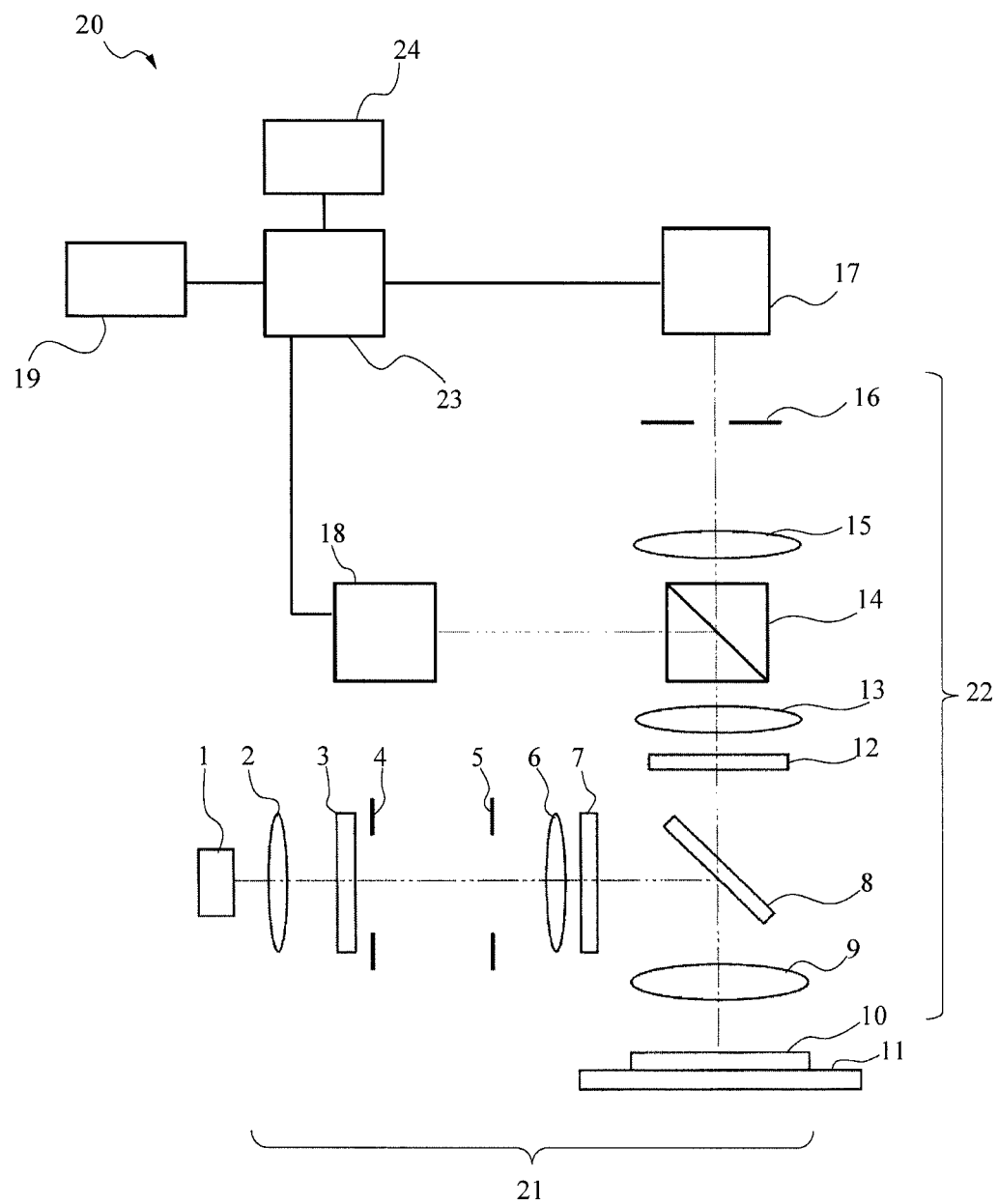
FIG. 1 is a schematic cross-sectional view illustrating a configuration of a defect inspection device.

Hereinafter, a preferred embodiment of the present invention will be described with reference to the accompanying drawings. FIG. 1 is a diagram illustrating an overview of a defect inspection device 20 which is an example of embodiment of the present invention and shows a schematic cross-sectional view within a plane passing through an optical axis.

The defect inspection device 20 is configured by including a light source 1, an illumination optical system 21 that radiates illumination light emitted from the light source 1 onto a wafer (substrate) 10 which is a sample placed on a stage 11 via an objective lens 9, a detection optical system 22 that condenses light reflected by the wafer 10, a first image pickup device 17 that detects a pupil image of the objective lens 9 of the image condensed by the detection optical system 22, a second image pickup device 18 that detects an image of the wafer 10, and a detection section 23 that detects a defect of the wafer 10 from the pupil image picked up by the first image pickup device 17.

The illumination optical system 21 has a condenser lens 2, an illuminance uniformalizing unit 3 including an interference filter, an aperture stop 4, a first field stop 5, a relay lens 6, a polarizer 7, a half mirror 8 and the objective lens 9 arranged on the optical axis from the light source 1 side in that order. Here, the illumination optical system 21 is configured such that the illumination light emitted from the light source 1 is reflected by the half mirror 8 and is then led to the wafer 10 via the objective lens 9. The optical axis of the illumination optical system 21 is arranged so as to substantially coincide with the optical axis of the detection optical system 22 to illuminate the wafer 10 with coaxial incident light. Furthermore, assuming the optical axis of this coaxial incident light illumination is the z-axis, axes that pass through the z-axis within the plane perpendicular to the z-axis, which are orthogonal to each other, are the x-axis and y-axis, the stage 11 is configured to be movable in the x-axis, y-axis and z-axis direction and rotatable around the z-axis.

On the other hand, the detection optical system 22 shares the half mirror 8 and the objective lens 9 with the illumination optical system 21, includes the objective lens 9, the half mirror 8, an analyzer 12, a first image forming lens 13, a half prism 14, a second image forming lens 15 and a second field stop 16 in order from the wafer 10 side and arranged on the optical axis in that order. Here, the light reflected by the wafer 10 is configured to pass through the half mirror 8 and be led to the first and second image pickup devices 17 and 18. Furthermore, the first image pickup device 17 is arranged at a position to detect light that has passed through the half prism 14 and the second image pickup device 18 is arranged at a position to detect light reflected by the half prism 14. In the detection optical system 22, the first image pickup device 17 is arranged at a position to detect the image of the pupil plane of the objective lens 9, that is, a position conjugate with the pupil plane of the objective lens 9, and the second image pickup device 18 is arranged at a position to detect the image of the wafer 10, that is, a position conjugate with the surface of the wafer 10. Furthermore, the second field stop 16 is arranged at a position conjugate with the surface of the wafer 10. By illuminating the second field stop 16 using a detachable illumination section (not shown) arranged on the first image pickup device 17 side and by picking up an image of the second field stop 16 reflected from the wafer 10 using the second image pickup device 18, the region on the wafer 10 detected by the first image pickup device 17 is converted to an image pickup position of the second image pickup device 18. The image of the pupil plane of the objective lens 9 and the image of the wafer 10 detected by the first and second image pickup devices 17 and 18 can be observed from a monitor 19 via the detection section 23. Therefore, when the image detected by the second image pickup device 18 is observed via the monitor 19, it is possible to confirm the position of the wafer 10 to which illumination light is radiated.

The polarizer 7 arranged in the illumination optical system 21 and the analyzer 12 arranged in the detection optical system 22 are configured to be detachable from the defect inspection device 20 and can be inserted or withdrawn on/from the optical axis according to the state of the observation target (wafer 10). In the following descriptions, the use of the defect inspection device in a state where the polarizer 7 and the analyzer 12 are withdrawn therefrom will be explained.

On the other hand, the apertures of the aperture stop 4 and the first field stop 5 have a structure that enables the size (especially, the diameter in the direction of a straight line connecting the optical axis and this aperture) and the position within the plane orthogonal to the optical axis to be changed. For this reason, when the position of the aperture of the aperture stop 4 is changed, the angle of incidence of the illumination light radiated onto the wafer 10 changes, and when the size and position of the aperture of the first field stop 5 are changed, the size (range of illumination) and the position of the illumination region of the radiated surface of the wafer 10 can be changed. When the size of the aperture of the aperture stop 4 is changed, the size of a diffraction image on the pupil plane can be changed.

In the defect inspection device 20 having such a configuration, illumination light emitted from the light source 1 is condensed by the condenser lens 2, and with illuminance uniformalized by the illuminance uniformalizing unit 3, is radiated onto the aperture stop 4. The illumination light that has passed through the aperture of the aperture stop 4, passes through the first field stop 5, is collimated by the relay lens 6, reflected by the half mirror 8 and guided to the objective lens 9. Here, the aperture stop 4 and the pupil plane of the objective lens 9 are arranged on both sides of the first relay lens 6 at positions corresponding to substantially twice the focal length of the first relay lens 6. Thus, the image of the aperture of the aperture stop 4 is formed on or in the vicinity of the pupil plane of the objective lens 9 and further condensed by the objective lens 9 and radiated onto the wafer 10. That is, the aperture stop 4 and the pupil plane of the objective lens 9 have a conjugate relationship.

Figure 2:
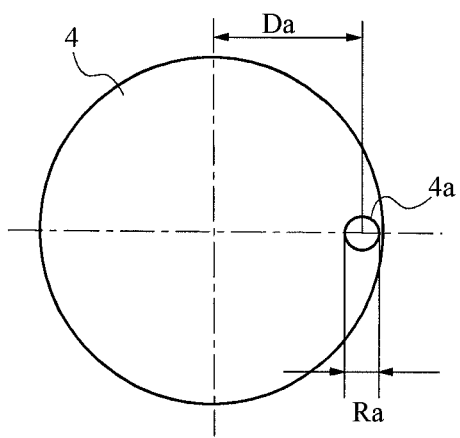
FIG. 2 is a diagram illustrating a configuration of an aperture stop; (a) illustrating an aperture stop in which a quasi-circular aperture is formed and (b) illustrating an aperture stop in which a quasi-rectangular aperture is formed.
Figure 2:
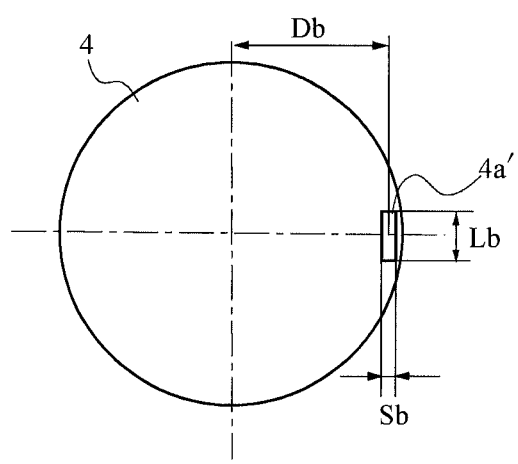
Figure 3:
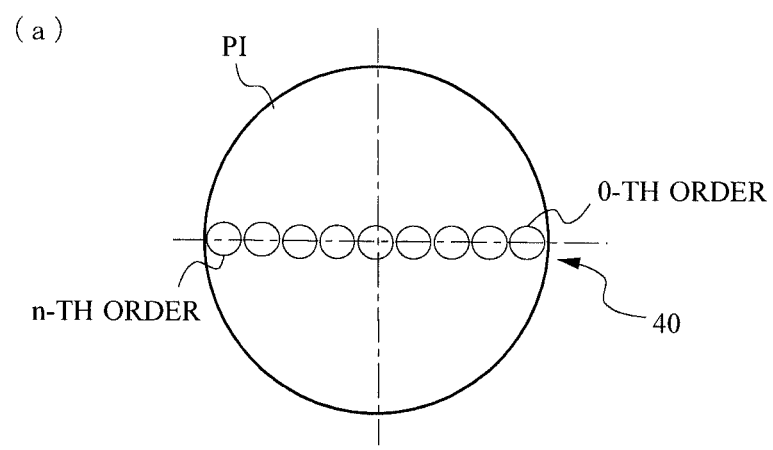
FIG. 3 is a diagram illustrating a pupil image of an objective lens in which an image of the aperture of the aperture stop shown in FIG. 2 is formed; (a) illustrating a case where the aperture stop in FIG. 2(a) is used and (b) illustrating a case where the aperture stop in FIG. 2(b) is used.
Figure 3:
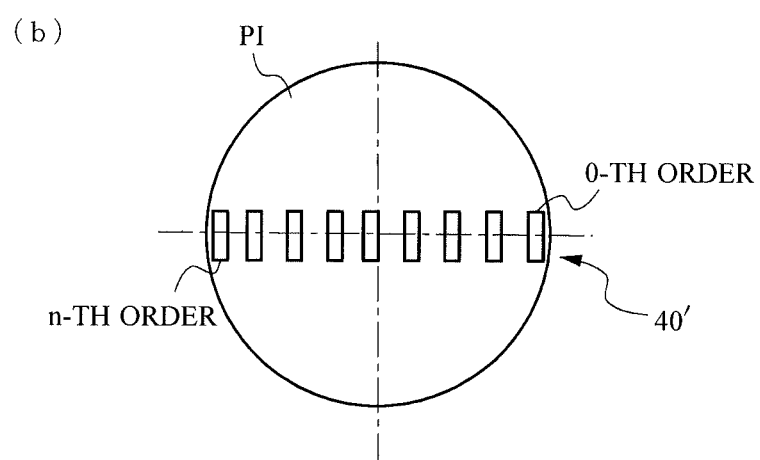

The illumination light radiated through the objective lens 9 onto the wafer 10 is reflected by the surface of the wafer 10 and condensed by the objective lens 9 again. In this case, the image of the aperture of the aperture stop 4 reflected by the wafer 10 is formed on the pupil plane of the objective lens 9 (or in the vicinity thereof), but diffracted light by a repeated pattern (inspection pattern inspected using the following method) formed on the wafer 10 is also generated and an image thereof is formed on the pupil plane likewise. Thus, when, for example, a circular aperture 4a as shown in FIG. 2(a) is formed in the aperture stop 4 in the vicinity of the outer circumferential portion of the aperture stop 4, as shown in FIG. 3(a), diffraction images 40 of the aperture 4a are formed side by side according to the order of diffraction in an order sequence on the pupil plane of the objective lens 9 (FIG. 3(a) illustrates an image PI of the pupil plane). The direction in which diffraction images 40 are arranged corresponds to a line where the plane including the optical axis and the center line of the illumination light tilted by the aperture stop 4 and the pupil plane cross each other. The diffraction image (reflected image) whose diffraction order is 0-th order is formed at a position (and range) corresponding to the aperture 4a of the aperture stop 4 on the pupil plane of the objective lens 9 and first order, second order . . . n-th order diffraction images are formed side by side as described above (FIG. 3(a)). In this case, the diameter of the aperture 4a of the aperture stop 4 is adjusted so that the diffraction images of the 0-th order (image by the reflected light) to n-th order do not overlap each other. For example, when the circular aperture 4a is formed in the aperture stop 4 as described above, the size of the aperture diameter (size) Ra of the aperture 4a is changed and adjusted so that the diffraction images formed on the pupil plane do not overlap each other.

To be more specific, by setting the aperture diameter (size) Ra of the aperture 4a of the aperture stop 4 so as to satisfy the condition shown in equation (1) below, it is possible to prevent neighboring diffraction images from overlapping each other on the pupil plane. Here, β denotes imaging magnification between the aperture stop 4 and the pupil of the objective lens 9, P denotes a pitch of a repeated (inspection) pattern formed on the wafer 10 which is an inspection target, λ denotes a wavelength (inspection wavelength) of illumination light radiated onto the wafer 10 and f denotes a focal length of the objective lens 9.

$$Ra \leq |\beta| \times f \times \lambda/P \quad (1)$$

Here, assuming the wavelengths (inspection wavelengths) of the illumination light are three wavelengths of red (R), green (G) and blue (B), size Ra of the aperture 4a may be set so that equation (1) is satisfied with blue light (λ=440 nm) having the shortest wavelength. This is because the interval between images by diffracted light is also narrowed as the wavelength becomes shorter, and if the above condition is satisfied with the shortest wavelength, the condition can also be satisfied with longer wavelengths.

The shape of the aperture formed in the aperture stop 4 is not limited to a circular shape, but may be a rectangular shape as an aperture 4a' shown in FIG. 2(b). In this case, as with the above described circular aperture 4a, diffraction images 40' corresponding to different diffraction orders are formed side by side on the pupil plane (pupil image PI) of the objective lens 9 in this order sequence as shown in FIG. 3(b). Furthermore, in this case, by adjusting a length Sb of a side extending in the direction of a straight line connecting the optical axis of the aperture 4a' and the aperture 4a' so as to satisfy equation (2) shown below, it is possible to adjust the diffraction images 40' formed side by side on the pupil plane so as not to overlap each other.

$$Sb \leq |\beta| \times f \times \lambda/P \quad (2)$$

Furthermore, when such a rectangular aperture 4a' is provided, a size Lb of a side extending in a direction orthogonal to the side indicated by the size Sb is preferably set to be greater than the size Sb. This is to secure a range of high luminance obtained in the center of the diffraction image since the luminance of the image of the aperture 4a' in such a shape gradually spreads in the direction orthogonal to the direction in which the illumination light impinges on the sample surface from the center. Hereinafter, a case will be described where the aperture stop 4 having the circular aperture 4a is used.

In this defect inspection device 20, the position at which illumination light is radiated onto the surface of the wafer 10 is adjusted by moving the stage 11 in the x- and y-axis directions, the angle at which the illumination light is radiated is adjusted by adjusting the position and size of the aperture stop 4 and the aperture of the first field stop 5 as described above and the direction in which the illumination light is radiated with respect to the cycle direction of the repeated pattern (inspection pattern) formed on the wafer 10 which is the inspection target (azimuth of illumination light with respect to repeated pattern) is adjusted by rotating the stage 11. Furthermore, when the surface of the wafer 10 is moved to the focus of the objective lens 9, the movement is adjusted by moving the stage 11 in the z-axis direction. Furthermore, the wavelength region of the illumination light is adjusted using an interference filter of the illuminance uniformalizing unit 3.

When the defect inspection device 20 is configured as described above, by picking up the pupil image PI formed on the pupil plane (or in the vicinity thereof) of the objective lens 9 using the first image pickup device 17, it is possible to detect diffraction images of a plurality of orders of the aperture 4a of the aperture stop 4 formed on the pupil plane of the objective lens 9 after being reflected on the surface of the wafer 10 and the detection section 23 can decide the quality of the repeated pattern (inspection pattern) formed on the wafer 10 which is the inspection target using the diffraction images of the plurality of orders. That is, the pupil image of the wafer made up of a conforming item pattern whose image is picked up by the first image pickup device 17 (hereinafter, a wafer having a conforming item pattern will be referred to as "conforming item sample") is stored in the storage section 24 connected to the detection section 23 as a reference image, the reference image is read by the detection section 23, the pupil image of the wafer 10 which is the inspection target is detected as a detected image, the detected image is compared with the reference image and the difference is detected and a defect of the wafer 10 which is the inspection target is thereby detected. As for the method of inspecting a defect by the detection section 23, a defect may be decided, for example, by comparing differences in gradation values per pixel between the reference image and the detected image (since the luminance value in the pupil image is detected as a plurality of levels of gradation (digital amount), referred to as "gradation value" in the following descriptions) and deciding the presence of a defect when the difference in a certain pixel exceeds a predetermined threshold. Thus, the quality of the wafer 10 is decided by calculating a luminance value (gradation value) of the image of the pupil plane of the objective lens 9 by the wafer 10 and comparing the luminance value with a reference value of a conforming item sample stored beforehand, and therefore the quality can be measured in a short time.

Figure 4:
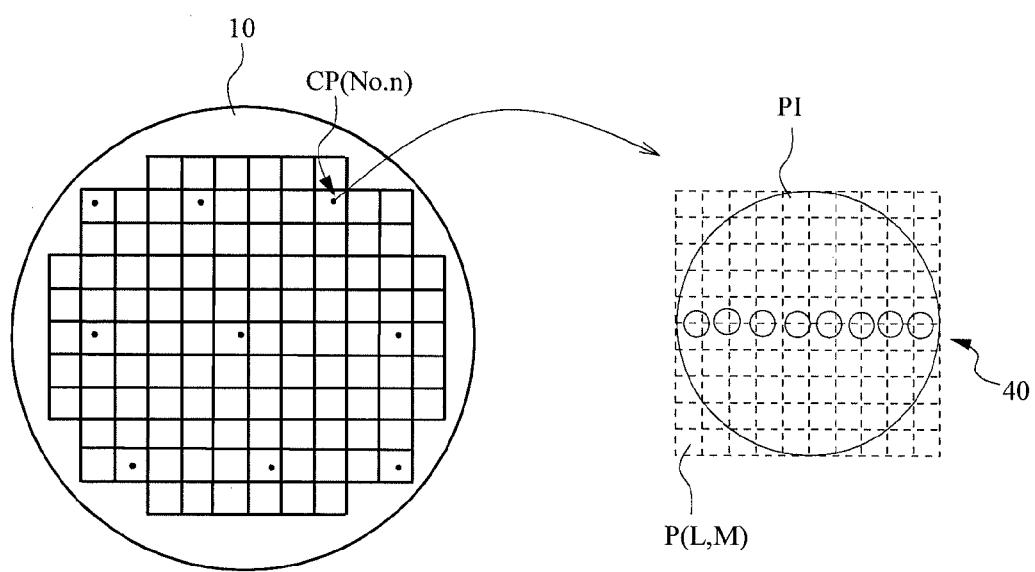
FIG. 4 is a diagram illustrating inspection points on a wafer and a method of dividing a pupil image.

Not all pixels need to be compared, but only a predetermined number of pixels may be used as comparison targets as will be described below. First, a method of determining the position of a pixel which is an inspection target in the image PI (pupil image at a predetermined position CP) of the pupil plane which becomes a comparison target (this will be referred to as "optimum position" in the following explanations) will be described. Here, suppose the optimum position indicates, when the pupil image PI is divided into a plurality of areas P(L,M) (L×M-partitioned area) beforehand as shown in FIG. 4, to what part of the area the position corresponds. As the method of determining the optimum position, using a wafer in which a repeated pattern having different line widths from a conforming item range which is an evaluation substrate to a defective item range exists (e.g., a wafer including a repeated pattern having different line widths from the above described conforming item range to the defective item range exists by exposing the interior of the wafer with different amounts of exposure, and hereinafter called "test wafer"), the predetermined position CP including a repeated pattern having different line widths from the above described conforming item range to the defective item range of the test wafer is measured using reference measuring means and a measured value is acquired. The defect inspection device 20 shown in the present embodiment radiates illumination light to a position corresponding to the predetermined position CP on the test wafer where the repeated pattern having different line widths from the conforming item range to the defective item range exists, calculates a gradation value (luminance value) for each area by picking up a pupil image of the predetermined position CP, obtains a correlation between the aforementioned measured value and each gradation value (luminance value) and determines an area having the highest correlation as an optimum position. A case will be described here where CD-SEM is used as the reference measuring means (furthermore, the measured value by the CD-SEM will be referred to as "CD-SEM value"). Suppose the CD-SEM value of the test wafer in this case is measured and stored beforehand in the storage section 24.

To be more specific, the test wafer is placed on the stage 11 of the defect inspection device 20, a gradation value (luminance value) per area of the pupil image PI at the predetermined position CP on the test wafer (point CP on the wafer 10 shown in FIG. 4) is calculated and a correlation between the gradation value and the CD-SEM value corresponding to the aforementioned predetermined point CP out of the CD-SEM values of the test wafer stored in the storage section 24 is determined for each area.

For example, the image PI of the pupil plane detected by the first image pickup device 17 for each inspection point CP (No. 1 to No. n) within the plane of the test wafer is divided, for example, into 45×45 areas P and set. An image of the diffracted light from the test wafer is formed on the image PI of the pupil plane and the first image pickup device 17 is detected as such a diffraction image (pupil image) 40 as shown, for example, in FIG. 3(*a*). A correlation between the gradation value (luminance value) of the pupil image PI and CD-SEM value within the set areas P(0,0) to P(45,45) is determined. FIG. 5(*a*) illustrates a correspondence table 100 of CD-SEM values (SEM) at inspection points CP (No. 1 to No. n) within the plane of the test wafer and gradation values (luminance values) in arbitrary areas P(L,M) on the pupil plane (image surface PI) and this correspondence table 100 is stored in the aforementioned storage section 24. Here, each inspection point CP (No. 1 to No. n) set within the plane of the test wafer is set in an inspection point column 100a. A CD-SEM value at each inspection point CP is stored in a SEM column 100b. Furthermore, a gradation value (luminance value) in an arbitrary area P(L,M) on the pupil plane at each inspection point CP when an inspection wavelength (illumination wavelength) R is set in a gradation value R column 100c, an inspection wavelength (illumination wavelength) G is set in a gradation value G column 100d, and an inspection wavelength (illumination wavelength) B is set in a gradation value B column 100e, is stored in the respective columns. This result gives a correlation coefficient 100f (CR(L,M), CG(L,M), CB(L,M)) between a gradation value of an arbitrary area P(L,M) on the pupil plane at the inspection point CP and the CD-SEM value when each inspection wavelength (illumination wavelength) is used.

This correlation coefficient is obtained by assuming the pupil image obtained at each inspection point CP (No. 1 to No. n) as a correlation coefficient CR(L,M), CG(L,M), CB(L, M) of each inspection wavelength in each area P(0,0) to P(N,N) and is stored in the correlation function table 101 of the storage section 24. This correlation function table 101 has a data structure as shown in FIG. 5(*b*), and areas P(0,0) to P(N,N) on the pupil image PI obtained at the point CP are set in an area column 101*a* on the pupil image, and a correlation coefficient of the gradation value (luminance value) with an inspection wavelength R in the area P is stored in a gradation value R column 101*b*. Likewise, correlation coefficients of gradation values G and B with inspection wavelengths G and B are stored in a gradation value G column 101*c* and in a gradation value B column 101*e*, respectively.

Here, since the position of a diffraction image formed on the pupil plane varies with each inspection wavelength, it is preferable to adjust, for each wavelength, the way the pupil image PI is divided. As described so far, an area P(Xf, Yf) of the pupil plane where a correlation value obtained from a correlation coefficient in each wavelength calculated as shown in FIG. 5(*b*) becomes a maximum is determined as an optimum position.

Figure 6:
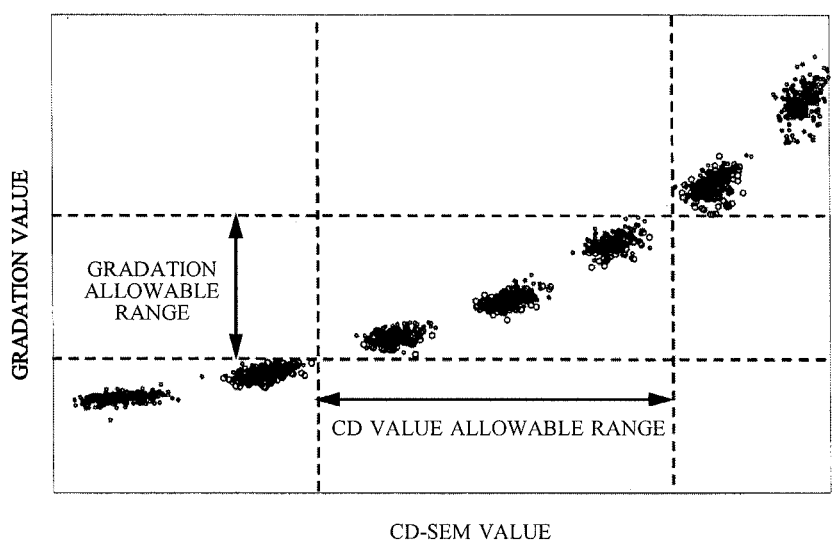
FIG. 6 is a schematic diagram illustrating a relationship between a CD-SEM value and a gradation value, and an allowable range thereof.

Next, a relationship between a gradation value in the area P(Xf,Yf) of the pupil image PI where the correlation becomes a maximum and the CD-SEM value is expressed as a graph as shown in FIG. 6, and an allowable range in a gradation value at an optimum position of the pupil image measured by the defect inspection device 20 is determined from the allowable range in the CD-SEM value of the test wafer measured by the CD-SEM. FIG. 6 shows an inspection example when the inspection pattern formed on the wafer 10 is a hole pattern and the CD-SEM value and the gradation value are approximated by a quadratic function.

When the above described configuration is adopted, it is possible to place the wafer 10 which is the inspection target on the stage 11, pick up the pupil image PI using the first image pickup device 17, calculate a gradation value (luminance value) at the optimum position on this pupil image PI by the detection section 23 and inspect whether or not the gradation value falls within the aforementioned allowable range, and thereby decide, when the gradation value falls within the allowable range, that the repeated pattern formed on the inspection target wafer 10 is a conforming item and decide, when the gradation value is outside the allowable range, that the inspection target wafer 10 is a defective item.

Here, it is preferable to adjust light quantity of the light source 1 so that the gradation value (intensity) of the diffraction image 40 formed on the pupil image PI does not saturate. This is because the diffracted light is weakened as the order of diffracted light increases from the 0-th order to a higher order and the gradation value (luminance value) of the high-order diffraction image decreases accordingly. For example, when the light quantity of the light source 1 is adjusted to match the 0-th order diffracted light, the gradation value of the diffraction image is too low to be measured because the high-order diffracted light is weak. On the contrary, when the light quantity of the light source 1 is adjusted to match the high-order diffracted light, the 0-th order diffracted light is strong and the gradation value (luminance value) of the diffraction image is saturated and cannot further be measured. For this reason, it is preferable to adjust and set the light quantity of the light source 1 depending on the order of diffracted light whose diffraction image is used to perform an inspection according to the optimum position P(Xf, Yf).

Thus, by determining an optimum position to calculate a luminance value for an image of the pupil plane picked up using the first image pickup device 17 and detecting a defect with the luminance value at the position, it is possible to detect the defect of the wafer 10 efficiently in a short time.

Based on a correlation between a measured value of a test wafer measured by reference measuring means, for example, CD-SEM and luminance values in a plurality of areas in the pupil image of the test wafer picked up by the first image pickup device 17, this optimum position corresponds to a position (area) with a high correlation, and it is thereby possible to perform a defect inspection more efficiently and decide the quality in a short time.

A case with the defect inspection device 20 has been described so far where the illuminance uniformalizing unit 3 is configured by including an interference filter that selects a wavelength of illumination light emitted from the light source 1 and radiated onto the wafer 10, but the illuminance uniformalizing unit 3 may also be configured so as not to include the interference filter. Furthermore, by arranging an optical path splitting element, a color filter or the like between the first image pickup device 17 and the second field stop 16 and configuring the first image pickup device 17 with a plurality of image pickup devices, it is possible to observe the pupil image divided into wavelength regions of R, G and B.

Figure 7:
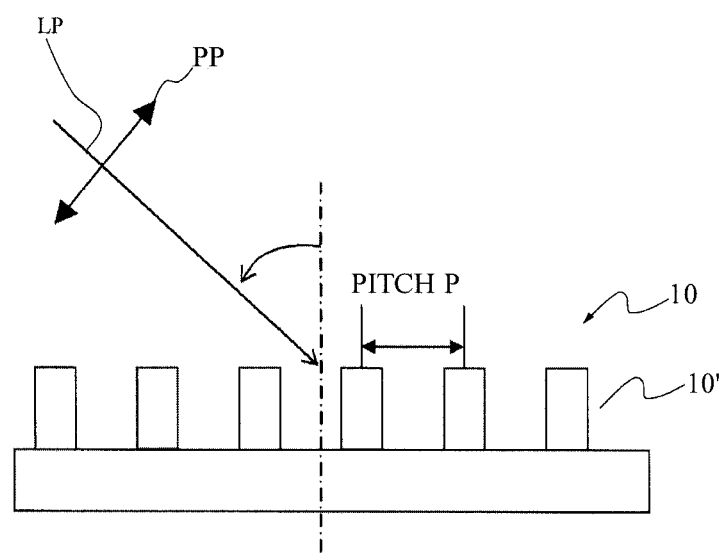
FIG. 7 is a schematic diagram when a wafer surface pattern is illuminated with P polarization in a pitch direction thereof.
Figure 8:
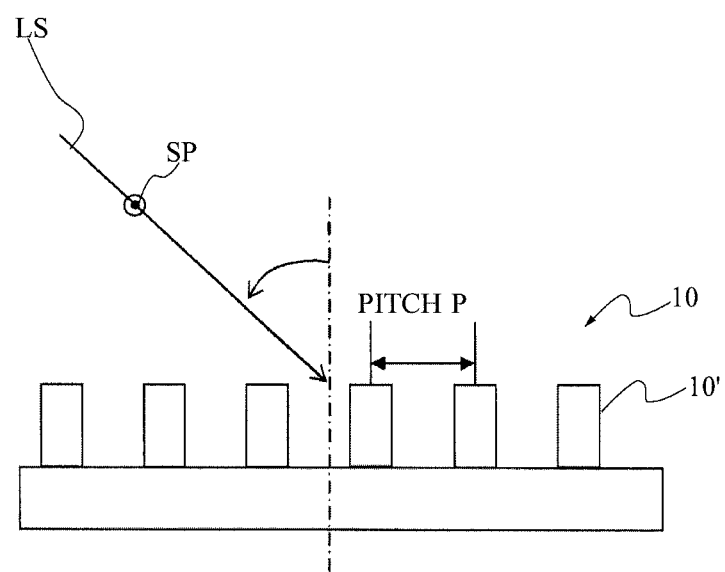
FIG. 8 is a schematic diagram when a wafer surface pattern is illuminated with S polarization in a pitch direction thereof.

Furthermore, a defect inspection in which no particular polarization processing is performed on the light from the light source 1 has been described above, but an inspection may be performed using only light of an S-polarization component or only light of a P-polarization component as the illumination light radiated onto the wafer 10. That is, since the detachable polarizer 7 is provided, linear polarization can be uniformly used as the illumination light. FIG. 7 illustrates a case where the polarizer 7 is rotated with respect to the light from the light source 1 and the light is impinged as P-polarization with respect to the direction of the pitch P of a pattern 10' formed on the wafer 10 (incident light LP) and FIG. 8 illustrates a case where the polarizer 7 is rotated and the light is impinged as S-polarization with respect to the direction of the pitch P of the pattern 10' formed on the wafer 10 (incident light LS). The double arrow that intersects the incident light LP in FIG. 7 at a right angle represents a vibration direction PP of linear polarization and it is a vibration direction PS of linear polarization that intersects the incident light LS in FIG. 8 at a right angle and is expressed as directing from back to front. Performing an inspection using only the light of the respective polarization components in this way makes it possible to remove influences (noise) further below (the base of) the pattern 10' formed on the surface of the wafer 10. That is, depending on the polarization component, the reflection characteristic differs due to the noise component caused by influences of the base, and it is possible to adopt such a defect inspection device and method as to remove influences of the base using this difference.

The present embodiment calculates a correlation between a measured value of the test wafer measured using reference measuring means and luminance values at a plurality of positions in the image of the pupil plane of the objective lens of the test wafer picked up using the first image pickup device 17 and uses a luminance value at a position in the image of the pupil plane of the objective lens having a high correlation for measurement. However, it goes without saying that it is possible to determine an optimum position in the pupil where the correlation between a variation in size and shape of a pattern and a gradation variation in the pupil becomes highest through a vector analysis simulation beforehand using the angle of incidence of illumination and the polarization component as parameters and set a position (area) with a high correlation based on the correlation with luminance values in a plurality of areas in the pupil image of the test wafer picked up using the first image pickup device 17 of the present embodiment in a short time.

REFERENCE SINGS LIST

1 Light source 4 Aperture stop 4a Aperture 9 Objective lens 10 Wafer (substrate) 20 Defect inspection device 22 Detection optical system 23 Detection section 24 Storage section

The invention claimed is:

1. A defect inspection device that inspects a defect of a substrate on which a repeated pattern is formed, comprising:
an illumination optical system including
a light source that emits Illumination light, and
an aperture stop having an aperture through which the emitted illumination light passes so that the emitted illumination light is radiated onto the substrate to thereby be reflected by the substrate;
a detection optical system including an objective lens that condenses the light reflected by the substrate and thereby forms a pupil image on a pupil plane;
a receiver that receives, at a position where the pupil image on the pupil plane is formed by the detection optical system, diffracted light of a plurality of orders generated due to the repeated pattern formed on the substrate; and
a detector that detects a defect of the repeated pattern formed on the substrate based on a brightness of a portion of a detection region out of detection regions where the diffracted light is received by the receiver,
wherein at least one of a wavelength of the illumination light, a size of the aperture of the aperture stop, and a focal length of the objective lens is settable to separate the diffracted light of the plurality of orders on the pupil plane, wherein
the illumination light emitted by the light source passes through the objective lens to thereby be radiated onto the substrate,
the aperture stop is arranged at a position conjugate with the pupil plane, and
the aperture of the aperture stop is configured to be enabled to change the position and aperture diameter within a plane orthogonal to an optical axis of the illumination optical system.

2. The defect inspection device according to claim 1, wherein the portion of the detection region is a region of a pupil image generated by diffracted light of any one order out of the diffracted light of a plurality of orders.

3. The defect inspection device according to claim 2, further comprising a storage that stores a reference value,
wherein the detector reads the reference value from the storage, compares the reference value with the brightness which is calculated from the pupil image and thereby detects a defect of the repeated pattern formed on the substrate.

4. The defect inspection device according to claim 2, wherein
the portion of the detection region is a region where a correlation of a difference of the repeated pattern and the brightness is large, and
the detector is configured so as to detect a defect of the repeated pattern formed on the substrate according to the brightness at the portion of the detection region.

5. The defect inspection device according to claim 4, further comprising:
a device which, for the portion of the detection region, calculates a correlation between a measured value of an evaluation substrate on which a plurality of repeated patterns having different levels of quality are formed and the brightness of the pupil image by the diffracted light of the plurality of orders by the evaluation substrate for each order, and determines a pupil image region by an order of diffracted light with the high correlation.

6. The defect inspection device according to claim 1, wherein the illumination optical system comprises a wavelength selector that selects a wavelength region of the illumination light emitted by the light source and radiated onto the repeated pattern formed on the substrate.

7. The defect inspection device according to claim 1, wherein the illumination optical system comprises a polarizer that polarizes the illumination light emitted by the light source and radiated onto the repeated pattern formed on the substrate to a predetermined linear polarization state.

8. The defect inspection device according to claim 1, wherein the aperture stop is arranged at a position conjugate with the pupil plane and the illumination optical system is configured so as to satisfy the condition of:

$$Ra \leq |\beta| \times f \times \lambda / P$$

where the length of the aperture of the aperture stop in the direction of a straight line connecting an optical axis of the illumination optical system and the aperture is Ra, imaging magnification between the aperture stop and pupil of the objective lens is $\beta$, wavelength of light radiated onto the repeated pattern formed on the substrate is $\lambda$, pitch of the repeated pattern is P and the focal length of the objective lens is f.

9. The defect inspection device according to claim 1, wherein said at least one of the wavelength of the illumination light, the size of the aperture of the aperture stop, and the focal length of the objective lens is settable to separate the diffracted light of the plurality of orders so that the separated diffracted light of the plurality of orders do not overlap on the pupil plane.

10. A method of inspecting a defect of the substrate on which a repeated pattern is formed, comprising:
receiving diffracted light of a plurality of orders generated due to the repeated pattern at a position where a pupil image on a pupil plane is formed by a detection optical system, the received diffracted light of the plurality of orders being separated on the pupil plane, the detection optical system including an objective lens and forming the pupil image on the pupil plane by using the objective lens to condense light from the substrate; and
detecting a defect of the repeated pattern of the substrate based on a brightness at a portion of a detection region out of regions where the diffracted light of the plurality of orders is received in said receiving,
the method further comprising:
radiating light emitted from a light source of an illumination optical system onto the repeated pattern formed on the substrate via an aperture stop and the objective lens prior to said receiving, to thereby cause light to be reflected by the substrate, the reflected light being said light condensed by the objective lens, the aperture stop having an aperture through which the emitted illumination light passes, the aperture stop being arranged at a position conjugate with the pupil plane, and the aperture of the aperture stop being configured to be enabled to change the position and aperture diameter within a plane orthogonal to an optical axis of the illumination optical system.

11. The defect inspection method according to claim 10, wherein the portion of the detection region is a region of a pupil image generated by diffracted light of any one order out of the diffracted light of a plurality of orders.

12. The defect inspection method according to claim 11, wherein said detecting is configured so as to compare a conforming reference value with a brightness obtained in said receiving and thereby detect a defect of the repeated pattern formed on the substrate.

13. The defect inspection method according to claim 11, wherein
the portion of the detection region is a region where a correlation of a difference of the repeated pattern and the brightness is large, and
said detecting is configured so as to detect a defect of the repeated pattern formed on the substrate according to the brightness of the portion of the detection region obtained in said receiving.

14. The defect inspection method according to claim 13, wherein,
calculating, for the portion of the detection region, a correlation between a measured value of an evaluation substrate on which a plurality of repeated patterns having different levels of quality are formed and the brightness of the pupil image by the diffracted light of the plurality of orders by the evaluation substrate for each order, and determining a pupil image region by an order of diffracted light with the high correlation.

15. The defect inspection method according to claim 10, wherein the received diffracted light of the plurality of orders do not overlap on the pupil plane.

16. A defect inspection device that inspects a defect of a substrate on which a repeated pattern is formed, comprising:
a detection optical system including an objective lens that condenses light from the substrate;
a receiver that receives diffracted light of a plurality of orders generated due to the repeated pattern of the substrate at a position where a pupil image generated at a pupil plane of the detection optical system is formed; and
a detector that detects a defect of the repeated pattern of the substrate based on a brightness of a portion of a detection region out of detection regions where the diffracted light of the receiver is detected, wherein
the portion of the detection region is a region of a pupil image generated by diffracted light of any one order out of the diffracted light of a plurality of orders,
the portion of the detection region is a region where a correlation of a difference of the repeated pattern and the brightness is large,
the detection section is configured so as to detect a defect of the repeated pattern of the substrate according to the brightness at the portion of the detection region, and
for the portion of the detection region, a correlation between a measured value of an evaluation substrate on which a plurality of repeated patterns having different levels of quality are formed by reference measuring device and the brightness of the pupil image by the diffracted light of the plurality of orders by the evaluation substrate is calculated for each order and a pupil image region by an order of diffracted light with the high correlation is determined.

17. A defect inspection device that inspects a defect of a substrate on which a repeated pattern is formed, comprising:
a detection optical system including an objective lens that condenses light from the substrate;
a receiver that receives diffracted light of a plurality of orders generated due to the repeated pattern of the substrate at a position where a pupil image generated at a pupil plane of the detection optical system is formed;
a detector that detects a defect of the repeated pattern of the substrate based on a brightness of a portion of a detection region out of detection regions where the diffracted light of the receiver is detected; and
an illumination optical system including the objective lens that radiates light from a light source onto the repeated pattern formed on the substrate via the objective lens,
wherein the illumination optical system comprises an aperture stop at a position conjugate with the pupil plane and the illumination optical system is configured so as to satisfy the condition of:

$$Ra \le |\beta| \times f \times \lambda / P$$

where the length of an aperture of the aperture stop in the direction of a straight line connecting an optical axis of the illumination optical system and the aperture is Ra, imaging magnification between the aperture stop and a pupil of the objective lens is $\beta$, wavelength of light radiated onto the repeated pattern formed on the substrate is $\lambda$, pitch of the repeated pattern is P and a focal length of the objective lens is f.

18. A method of inspecting a defect of the substrate on which a repeated pattern is formed, comprising:
receiving diffracted light of a plurality of orders generated due to the repeated pattern at a position where a pupil image generated at a pupil plane of a detection optical system including an objective lens that condenses light from the substrate can be detected; and
detecting a defect of the repeated pattern of the substrate based on a brightness at a portion of a detection region out of regions where the diffracted light of the plurality of orders is received in said receiving, wherein
the portion of the detection region is a region of a pupil image generated by diffracted light of any one order out of the diffracted light of a plurality of orders,
the portion of the detection region is a region where a correlation of a difference of the repeated pattern and the brightness is large,
said detecting is configured so as to detect a defect of the repeated pattern formed on the substrate according to the brightness of the portion of the detection region obtained in said receiving, and
for the portion of the detection region, a correlation between a measured value of an evaluation substrate on which a plurality of repeated patterns having different levels of quality are formed by reference measuring device and the brightness of the pupil image by the diffracted light of the plurality of orders by the evaluation substrate is calculated for each order and a pupil image region by an order of diffracted light with the high correlation is determined.

19. A defect inspection device that inspects a defect of a substrate on which a repeated pattern is formed, comprising:
an illumination optical system including
a light source that emits Illumination light, and
an aperture stop having an aperture through which the emitted illumination light passes so that the emitted illumination light is radiated onto the substrate to thereby be reflected by the substrate;
a detection optical system including an objective lens that condenses the light reflected by the substrate and thereby forms a pupil image on a pupil plane;
a receiver that receives, at a position where the pupil image on the pupil plane is formed by the detection optical system, diffracted light of a plurality of orders generated due to the repeated pattern formed on the substrate; and
a detector that detects a defect of the repeated pattern formed on the substrate based on a brightness where at least some of the diffracted light of the plurality of orders is received by the receiver, wherein at least one of a wavelength of the illumination light, a size of the aperture of the aperture stop, and a focal length of the objective lens is settable to cause the diffracted light of the plurality of orders as received by the receiver to be separated on the pupil plane in accordance with the plurality of orders, the illumination light emitted by the light source passes through the objective lens to thereby be radiated onto the substrate, the aperture stop is arranged at a position conjugate with the pupil plane, and the aperture of the aperture stop is configured to be enabled to change the position and aperture diameter within a plane orthogonal to an optical axis of the illumination optical system.

* * * * *

UNITED STATES PATENT AND TRADEMARK OFFICE
CERTIFICATE OF CORRECTION

PATENT NO. : 8,705,840 B2
APPLICATION NO. : 13/096490
DATED : April 22, 2014
INVENTOR(S) : Endo Page 1 of 1

It is certified that error appears in the above-identified patent and that said Letters Patent is hereby corrected as shown below:

In the Claims

Column 11, Line 11, Claim 1, delete "Illumination" and insert -- illumination --, therefor.
Column 14, Line 54, Claim 19, delete "Illumination" and insert -- illumination --, therefor.

Signed and Sealed this
Twenty-second Day of July, 2014

Michelle K. Lee
*Deputy Director of the United States Patent and Trademark Office*